United States Patent
Wang

(10) Patent No.: US 6,277,135 B1
(45) Date of Patent: Aug. 21, 2001

(54) DRIVEN ROTARY INCISION SCALPEL

(76) Inventor: Kuen-Chyr Wang, No.9-30,80 Nong,Guan-In Lane, Hua-Tarn Hsiang, Chang-Hua Hsien (TW)

( * ) Notice: Subject to any disclaimer, the term of this patent is extended or adjusted under 35 U.S.C. 154(b) by 0 days.

(21) Appl. No.: 09/527,826

(22) Filed: Mar. 17, 2000

(51) Int. Cl.⁷ ................................................. A61B 17/20
(52) U.S. Cl. ........................ 606/179; 606/180; 600/566; 30/316
(58) Field of Search .............................. 606/1, 166, 167, 606/170, 171, 180, 179, 79–82; 600/562, 564, 566–568; 30/130, 301, 276

(56) References Cited

U.S. PATENT DOCUMENTS

| | | | |
|---|---|---|---|
| 3,618,611 | * | 11/1971 | Urban .................................... 606/170 |
| 4,137,920 | * | 2/1979 | Bonnet . |
| 5,230,154 | * | 7/1993 | Decker et al. . |
| 5,275,609 | * | 1/1994 | Pingleton et al. .................... 606/170 |
| 5,324,300 | * | 6/1994 | Elias et al. ............................ 606/179 |
| 6,039,748 | * | 3/2000 | Savage et al. ....................... 606/179 |
| 6,080,113 | * | 6/2000 | Heneveld et al. ................... 606/170 |

* cited by examiner

*Primary Examiner*—Henry J. Recla
*Assistant Examiner*—William Lewis
(74) *Attorney, Agent, or Firm*—Dougherty & Troxell

(57) ABSTRACT

A driven rotary incision scalpel having a pistol handle-shaped housing halves providing for mounting of a small form factor motor having a drive shaft. A gear on the front end of the drive shaft is enmeshed with the inner teeth of a ring gear of a two-stage reduction mount, which in turn drives a bevel gear that is enmeshed with a second driven bevel gear on a hollow rotary scalpel. When a trigger assembly is pulled backward and locked in, the outer barrel simultaneously moves to the rear, causing the front end of the hollow rotary scalpel to extend and switching on the motor that drives the blade at the front end into synchronous rotation.

3 Claims, 5 Drawing Sheets

DRIVEN ROTARY INCISION SCALPEL

BACKGROUND OF THE INVENTION

1) Field of the Invention

The invention herein relates to a driven rotary incision scalpel that, unlike similar instruments wherein the surgical incision blade is conjoined to the bottom end of the drive shaft tube, utilizes a small form factor motor mounted and concealed inside the lower end of a pistol grip-shaped housing which directly rotates a drive shaft at its front end and thereby achieves the driving of a hollow rotary scalpel. The scalpel is radially ensleeved at the upper section of the pistol grip-shaped housing, with the exterior of the rotary scalpel protected inside an active outer barrel. A trigger assembly is disposed at the lower extent of a center section such that pulling back the trigger with a finger, directly switches on the driving rotation to achieve precision and rapid rotary incision performance. A sliding arrestor block is situated at the interior surface of the trigger assembly and is capable of being selectively pulled initially to either the upper section position or lower section position by the finger of the user, thereby forming a rotary scalpel safety protection switch that prevents the trigger assembly from being pulled. The present invention achieves the concealment of the rotary scalpel incision motive force inside the housing to achieve convenient and lightweight flexible practicality.

2) Description of the Prior Art

A surgical operation is the most direct and effective method of remedying serious pathology of patients and, furthermore, is a widely utilized advanced medical treatment skill. However, due to technological progress, conventional knife-type operating tools utilized for internal surgery are being gradually replaced by new instruments or improved scalpels. Equipped with a pistol grip-shaped handle, the rotary scalpel 1 shown in FIG. 1 and FIG. 2 is a conventional instrument commonly utilized for endoscopic operations or for the removal of organs, polyps, and other tissue.

Referring to FIG. 1 and FIG. 2, the conventional rotary scalpel 1 is comprised of pistol grip-shaped shell halves 11, in which is disposed a hollow rotary scalpel 121, a frontal blade 1211, the inner section of which is mounted and retracted slightly inward in an inner barrel 122, the outer section of which is capable of retraction and extension. The frontal blade 1211 extends slightly outward from an active outer barrel 123. All of which constitutes a three-layer cylindrical scalpel body 12 sleeved on the inner section of the hollow rotary scalpel 121 is a rotatable driven bevel gear 13 engaging the driven bevel gear 14 which, by means of it being conjoined to the lower section of an extended drive shaft tube 15, is rotated by a center shaft 151, allowing the hollow rotary scalpel 121 to undergo high-speed rotary incision. Before the start of rotary incision with the hollow rotary scalpel 121 (as shown in FIG. 1), the operator must use a finger to pull back the trigger assembly 1231 on the outer barrel 123 to enable the barrel end to recede backward and allow the extension of the frontal blade 1211 from the hollow rotary scalpel 121 (as shown in FIG. 2) and thereby execute rotary incision operation.

The rotational driving force of such conventional rotary scalpels 1 typically consisted of an externally connected driving fixture 2 having an ON/OFF switch 21 that was not built into the said rotary scalpel 1. The driving fixture 2 utilized an internally installed motor (not shown in the drawing) connected to the shaft tube 15 that drove the center shaft 151 and rotated the driven bevel gear 14. A foot switch 21 was utilized at the same time to control the onset and termination of rotation.

As is obviously apparent, the driving shaft tube 15 was both a driven and a driving structural arrangement that provided for the union of an externally connected driving force and actually is an adaptation of an electric powered dentist drill. Both units are similar in terms of structure and operating procedure. However, the main difference was that the dental-application device could not accommodate the installation of active magnification medical treatment instrumentation which had a thin hollow opening smaller than the oral cavity. As such, the use of the said rotary scalpel 1 structure during actual medical treatment often resulted in the following operating constraints, which also adversely affected surgical quality and efficacy:

1. The rotation driving shaft tube 15 that enabled the rotary incision of the rotary scalpel 121 offered rotational capability, but due to the rotating center shaft line 151 contained inside it, the shaft tube 15 was of considerable thickness and hardness, which blocked and constrained the available working area of the chief operating surgeon and assisting personnel. Additionally, the operator could even be tripped by the said shaft tube 15 when changing position or moving the hands which could potentially disturb the operating position of the chief surgeon and result in dangerous procedural operating error or accidental injury. Of even greater importance, the extended length of the said shaft tube 15 directly affected the overall positional agility of the operating scalpel 1 and, furthermore, when the center shaft 151 was rotating within a lengthy tube, the large surface area of friction caused vibration and noise that negatively affected the operator and lessened practicality;

2. Under conditions wherein the center shaft 151 of the shaft tube 15 was rotated along a continuous length, if a bend or less than optimal rotational efficiency occurred at a certain point along the shaft tube 15, the center shaft 151 inside became incapable of rotating smoothly. This directly affected the rotational speed of the rotary scalpel 121 and, consequently, the operating procedure, often halting the operating procedure or precluding efficient completion;

3. The operator had to divert attention to placing the sole of the foot over a foot-operated switch in order to control the switching on or off of the rotary scalpel 121 and an inadequate degree of attentiveness often dangerously resulted in poor mechanical actuation or bad switch contact; and, 4. The inflexible arrangement that included a rotary scalpel 1 and an externally connected driving fixture 2 with a rotation driving shaft tube 15 conjoined to the center section was not only excessively large in terms of physical dimension, but given in addition of the great magnitude of friction on the center shaft 151, a motor with a higher torque capacity would have to be installed to provide sufficient rotational driving power, which resulted in larger overall physical specifications. In addition, since the rotary scalpel 1 was not removable, the entire assembly had to be sterilized after the completion of each operation. If the sterilization was not thorough, pathogenic transmission from the blade section to the next patient could occur during a future operation, a serious situation that could not be neglected.

In view of these situations, the inventor of the invention herein having actual familiarity and experience in the related fields conducted extensive innovative research to complete the present invention and submit it as a new patent application.

SUMMARY OF THE INVENTION

The primary objective of the invention herein is to provide a driven rotary incision scalpel in which a small form factor motor is mounted and thereby concealed at the lower section inside the pistol grip-shaped housing, with the motor directly rotating a drive shaft at its front end to achieve the driving of a hollow rotary scalpel radially ensleeved at the upper section of the pistol grip-shaped housing. As such, the invention precludes the utilization of a rotation driving shaft tube conjoined with the housing and, furthermore, does not require an externally connected driving force fixture. Thereby, the overall physical size is reduced and, since the conventionally equipped rotation driving shaft tube is no longer necessary, all associated procedural constraints during the operation process are eliminated, resulting in convenient and flexible operating performance.

Another objective of the invention herein is to provide a driven rotary incision scalpel in which the switching on and off of the hollow rotary scalpel is accomplished by a trigger assembly situated at the lower extent of the pistol grip-shaped main body. In addition to not diverting the attention of the operator to an external foot switch and allowing direct finger control of rotary incision onset and termination, this location allows the operator to avoid human error during rotary incision attributable to remote switching coordination. Furthermore, the driving motor is a low-torque requirement unit that, along with other advantages, produces less friction, vibration, and noise to assist in increasing surgical operation precision and safety.

Yet another objective of the invention herein is to provide a driven rotary incision scalpel which has been simplified by eliminating the externally connected driving fixture required by the conventional instrument, thereby significantly lowering the major portion of the structural production costs. As such, the invention herein is suitable as low cost structure for single-use disposable applications to prevent the occurrence of accidental disease transmission which provides for optimal medical treatment safety operating performance.

To enable a further understanding of the structural features, functions, and other capabilities of the present invention, the brief description of the drawings below is followed by the detailed description of the invention herein.

DETAILED DESCRIPTION OF THE INVENTION

Figure 1:
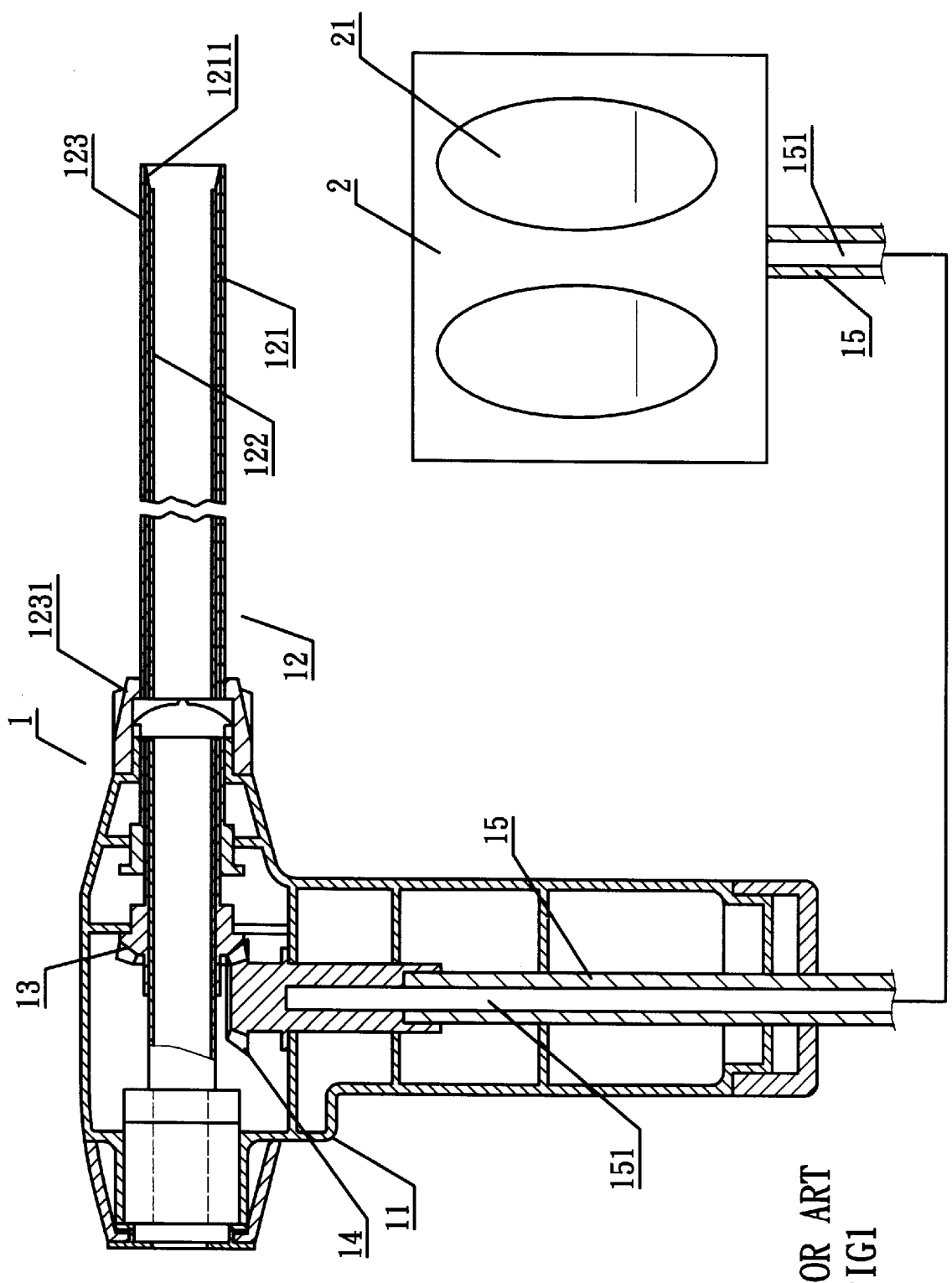
FIG. 1 is a cross-sectional view of a conventional rotary incision scalpel with the blade retracted.
Figure 2:
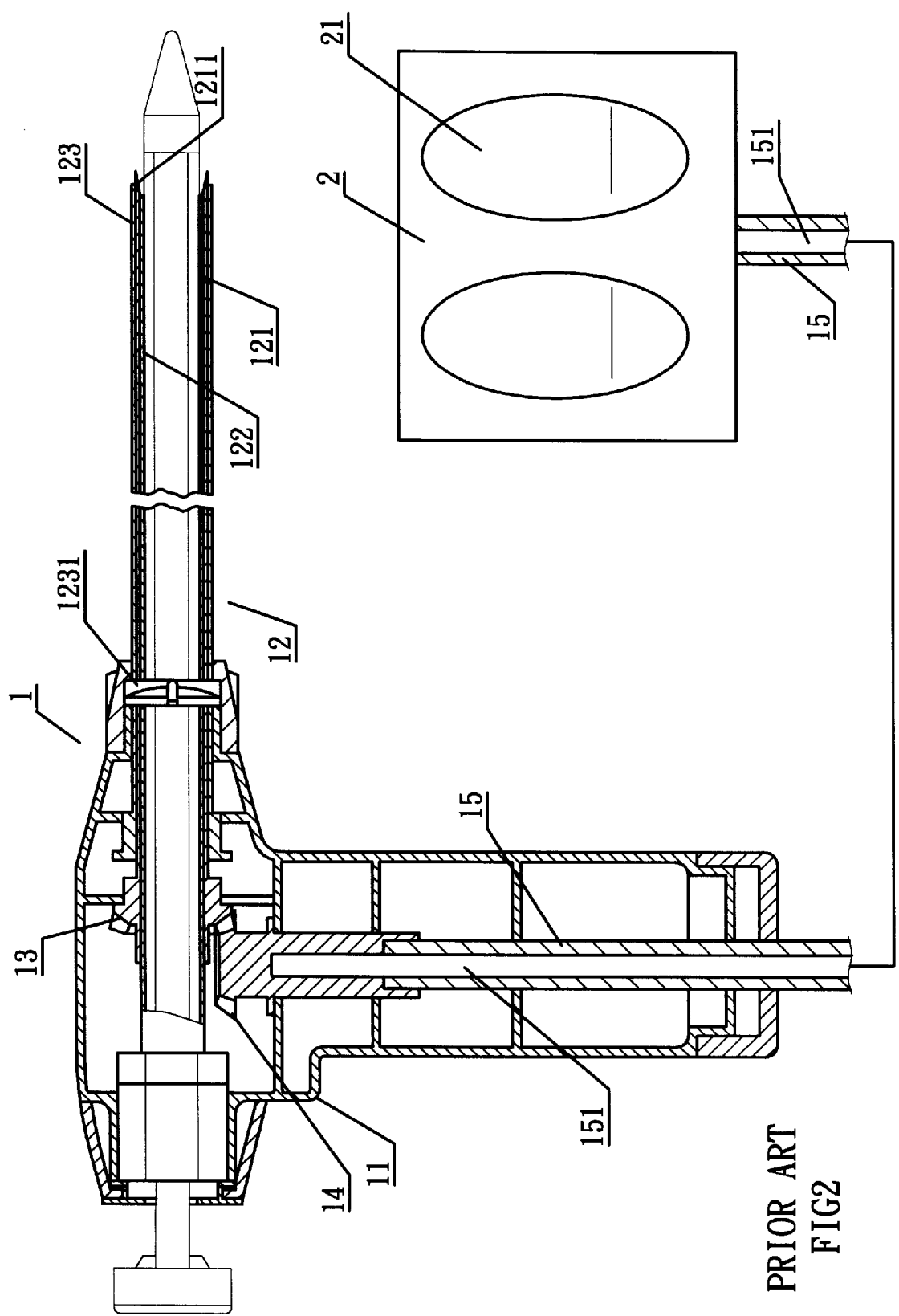
FIG. 2 is a cross-sectional view similar to FIG. 1 depicting the operation of the conventional rotary incision scalpel.
Figure 3:
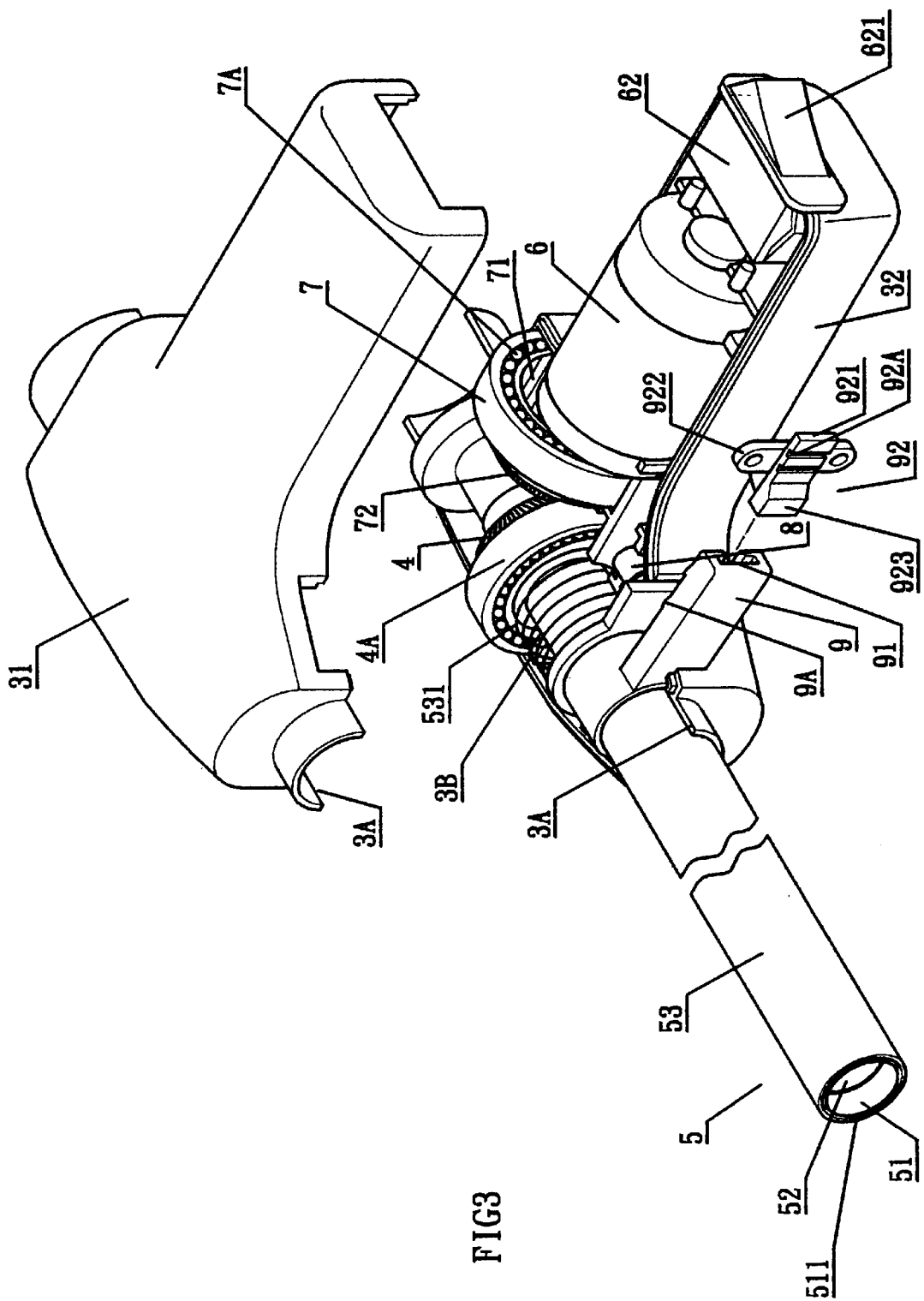
FIG. 3 is an exploded view of the present invention.
Figure 4:
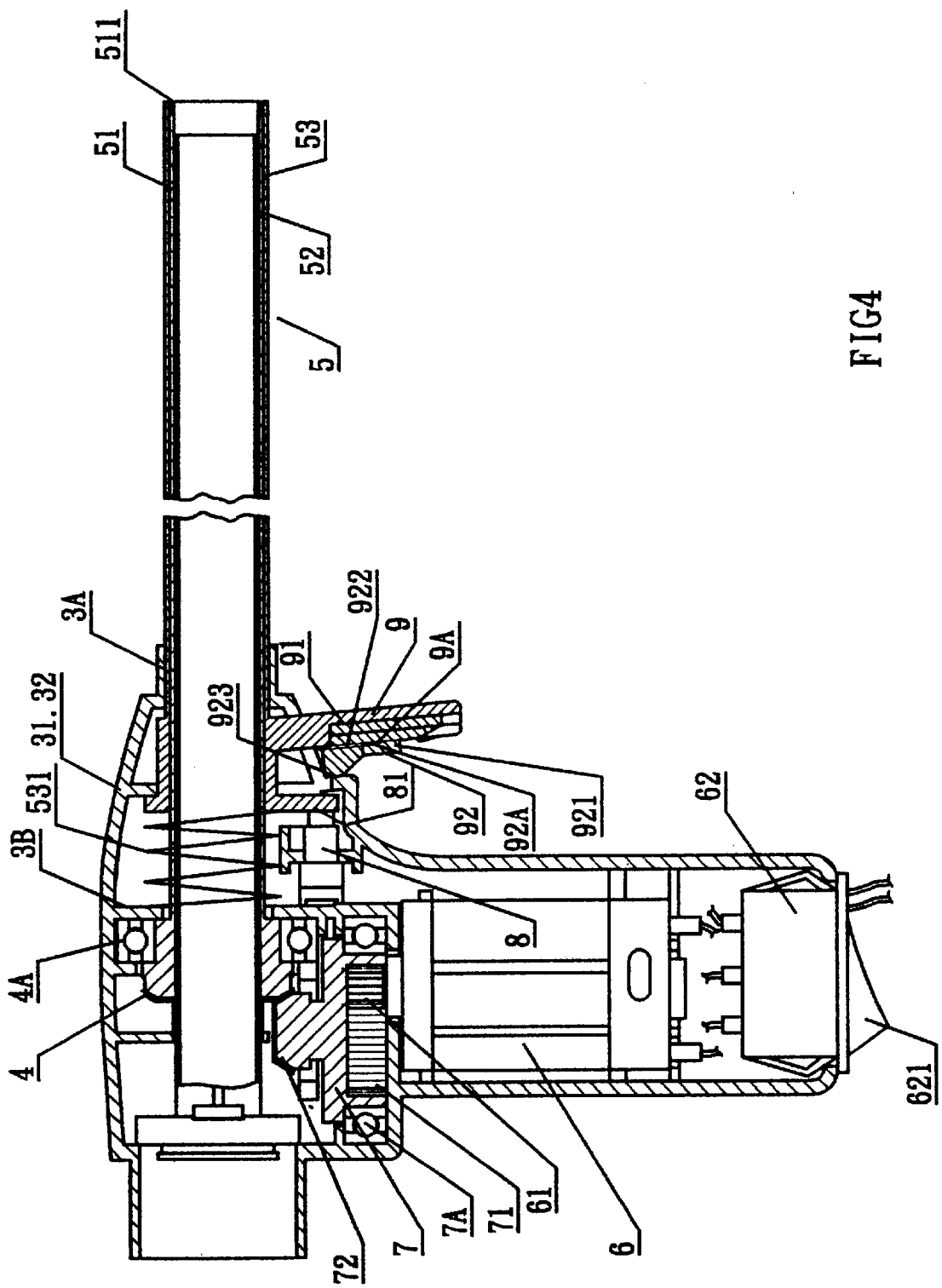
FIG. 4 is a cross-sectional view of the invention herein.

Referring to FIG. 3 and FIG. 4, the driven rotary incision scalpel of the present invention is comprised of a pair of matching pistol grip-shaped housing halves 31 and 32 with a sleeved hole 3A horizontally formed at the front tip of the said housing halves 31 and 32 to provide for the internal mounting of a hollow rotary scalpel 51. A blade 511 is disposed slightly inward within the front end of an inner barrel 52 and is capable of retraction and extension from the exterior section. The blade 511 at the front end is also capable of extending slightly outward from an active outer barrel 53. All of this structure constitutes a three-layer cylindrical scalpel body 5, wherein a rear section of the outer barrel 53 extends into the sleeved hole 3A. An annular compression spring 531 is positioned around the outer circumference of the hollow rotary scalpel 51 that holds the rear extent of the outer barrel 53 inside a chuck band 3B at the center section of the housing halves 31 and 32. This enables the outer barrel 53 to be normally pushed outward beyond the blade 511 at the front end of the hollow rotary scalpel 51 to thereby serve as a protective covering. Sleeved around the outer circumference at the interior section of the hollow rotary scalpel 51 is a bearing 4A positioning a rotationally driven bevel gear 4 such that the said driven bevel gear 4 is engaged to a rotating force applied from the rear and to thereby rotate the hollow rotary scalpel 51.

A small form factor motor 6 is internally mounted at the bottom section of the housing halves 31 and 32, with a gear 61 on the drive shaft of the said motor 6 enmeshed with the inner teeth of a ring gear 7 at the lower section of a two-stage reduction mount 7 situated at the upper extent of bearing 7A. The bevel gear 72 at the upper extent of the two-stage drive mount 7 is enmeshed with the driven bevel gear 4 to rotate the hollow rotary scalpel 51 and thereby synchronously impelling its rotary incision action.

A trigger assembly 9 projects from the lower center section of the housing halves 31 and 32 form which the active outer barrel 53 extends. The top section and rear extent of the said trigger assembly 9 is capable, when pulled and thereby moved towards the rear, of reaching a symmetrical area inside the housing halves 31 and 32, as well as the front end of the contact point 81 of a contact switch 8 that places a power supply in continuity with the motor 6 to enable its operation.

Figure 5:
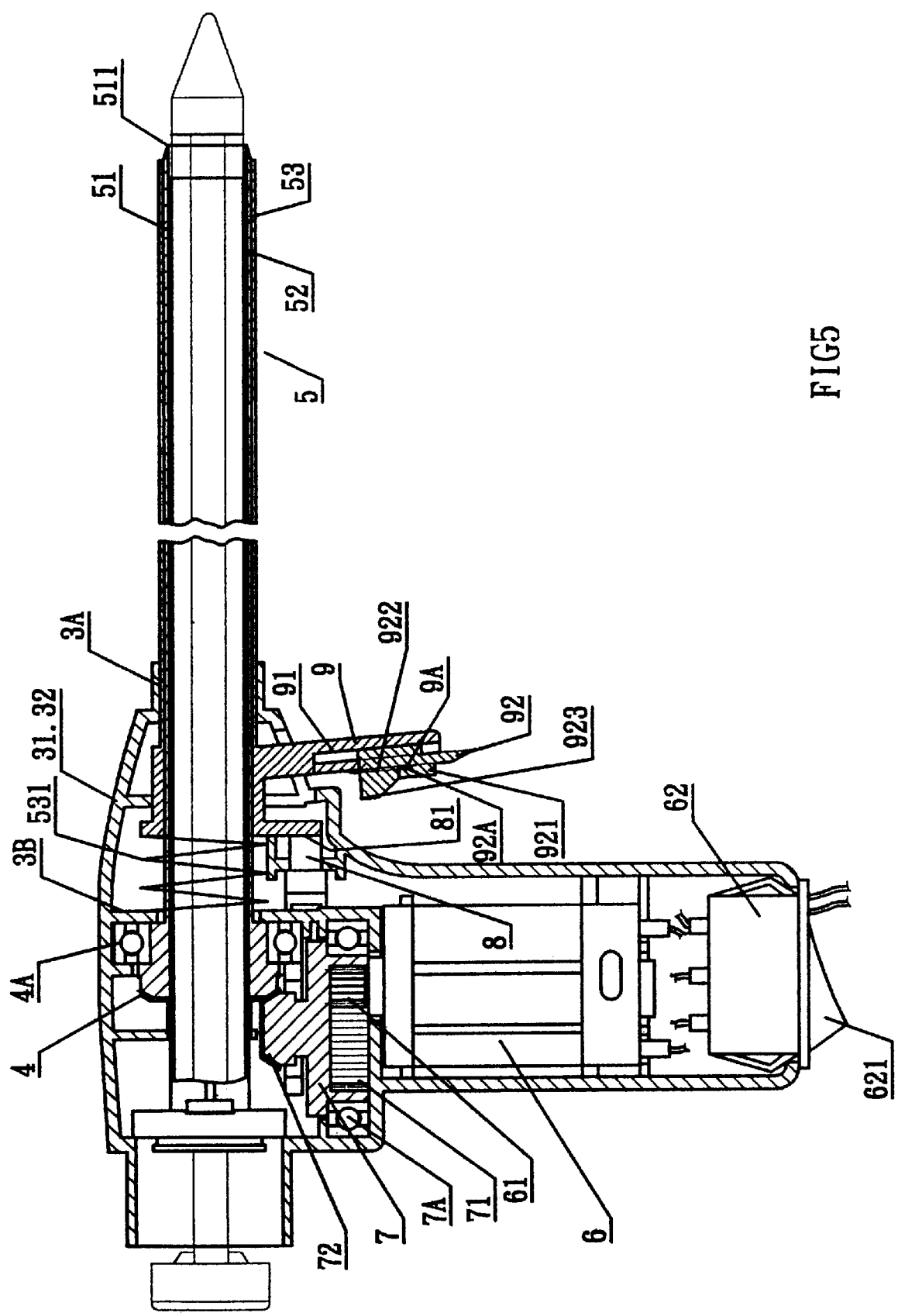
FIG. 5 is a cross-sectional view similar to FIG. 4 depicting the operation of the driven rotary incision scalpel herein.

In operation, after the operator extends the scalpel body 5 into the afflicted region of the patient, the trigger assembly 9 is pulled towards the rear and locked back (as shown in FIG. 5). At the same time, the outer barrel 53 moves backward and causes the blade 511 at the front end of the hollow rotary scalpel 51 to extend outward. When the trigger assembly 9 is locked back at the farthest extent of its travel, the front end of the contact point 81 of the said contact switch 8 is activated to initiate the operation of the motor 6 that rotates the hollow rotary scalpel 51 and achieves immediate synchronous rotary incision in a convenient operation.

Referring to FIG. 3 and FIG. 4, power supply wiring is attached to the rear extent of the motor 6 and is routed to a power supply switch 62 at the lower extent inside of the housing halves 31 and 32. Protruding from the outer section of the power supply switch 62 and utilized to control the switching on and off of electric current is another control button 621 that provides for power supply management before the operation of the motor 6 is initiated.

Referring to FIG. 3 and FIG. 4, additionally formed along the inner surface of the trigger assembly 9 is a U-shaped guide slot 91 that provides for the placement of a symmetrically surfaced and similarly shaped slot block 921 and, furthermore, the insertion of the trigger support section 922 of a sliding arrestor block 92 that allows the user to squeeze the trigger support section 922 and thereby push the sliding arrestor block 92 vertically upwardly and downwardly to check movement. Positioned along the inner surface of trigger assembly 9 and the sliding arrestor block 92 are upper and lower section locking protrusion point 9A and a recess 92A that enables the sliding arrestor block 92 to be moved upward and, furthermore, when engaged in position at the upper section locking protrusion point 9A, the top section of a protruding arrestor block 923 becomes inserted into the opening between the trigger assembly 9 and the housing halves 31 and 32 to form a safety switch (as shown in FIG. 4) that prevents the trigger assembly 9 from being pulled such that even if the power supply switch 62 has been toggled on, the hollow rotary scalpel 51 remains operationally disabled.

However, when the sliding arrestor block 92 is pulled downward and engaged in position at the upper section locking protrusion point 9A, since the protruding arrestor block 923 at the top section is released from engagement with the top section of the trigger assembly 9, the trigger assembly 9 becomes operable and can be pulled backward allowing the hollow rotary scalpel 51 to be operated by toggling on the power supply switch 62.

In summation, the invention herein is a practical and completely improved structure compared to known rotary scalpels that provides ensured safety, convenience, precision surgical performance, and excellent utility.

What is claimed is:

1. A driven rotary incision scalpel comprising: a pistol handle-shaped housing having a sleeved hole horizontally formed at a front of the housing; a hollow rotary scalpel assembly mounted in the sleeved hole and including a blade disposed slightly inwardly within a front end of an inner barrel capable of retraction and extension from an exterior section, the blade capable of extending outwardly from a front end of an outer barrel, constituting a three-layer cylindrical scalpel body, wherein the outer barrel extends into the sleeved hole; an annular compression spring positioned around an outer circumference of the hollow rotary scalpel assembly holding the rear of the outer barrel inside a chuck band at a center section of the housing, the spring normally pushing the outer barrel outward beyond the blade at the front end of the said hollow rotary scalpel assembly to thereby serve as a protective covering; a first bearing sleeved around the outer circumference at an interior section of the hollow rotary scalpel assembly positioning a rotatable first bevel gear;

a small form factor motor internally mounted at a bottom section of the housing; a gear mounted on a shaft of the motor meshing with inner teeth of a ring gear of a two-stage reduction mount situated on a second bearing; a second bevel gear on the two-stage reduction mount meshing with the first bevel gear to rotate the hollow rotary scalpel assembly and thereby synchronously impelling rotary incision action;

a trigger assembly projecting from outer sides of a lower center section of the housing the trigger assembly having a top section and rear extent, such that when pulled and thereby moved towards a rear, the trigger assembly moves a front end of a contact point of a contact switch which places a power supply in continuity with the motor to enable operation of the motor, whereby at the same time the trigger assembly is pulled towards the rear and locked back, said outer barrel moves backward, causing the blade at the front end of the said hollow rotary scalpel assembly to extend outward and initiates the operation of the motor to rotate the hollow rotary scalpel assembly.

2. The driven rotary incision scalpel of claim 1, further comprising power supply wiring attached to a rear of the motor and connected to a power supply switch at a lower extent of and inside the housing, the power supply switch having a portion protruding from the housing to control the switching on and off of electric current to the motor.

3. The driven rotary incision scalpel of claim 2, wherein the trigger assembly further comprises a U-shaped guide slot in which is mounted a similarly shaped slot block and a sliding arrestor block such that, the sliding arrestor block is vertically movable to check movement of the trigger assembly; positioned along an inner surface of the trigger assembly and the sliding arrestor block are upper and lower section locking protrusion point and a recess that enable the sliding arrestor block to be moved upward such that, when engaged in position at the said upper section locking protrusion point, a top section of the arrestor block is inserted into an opening between the trigger assembly and the housing to form a safety switch that prevents the trigger assembly from being pulled such that even if the power supply switch has been toggled on, thereby preventing operation of the hollow rotary scalpel assembly, and when the sliding arrestor block is pulled downward and, engaged in position at the said lower section locking protrusion point, the top section of the sliding arrestor block is released from engagement with a top section of the trigger assembly, enabling the said trigger assembly to be pulled backward such that the hollow rotary scalpel assembly can be operated by toggling on the power supply switch.

* * * * *